(12) United States Patent
Kim

(10) Patent No.: US 12,178,965 B2
(45) Date of Patent: *Dec. 31, 2024

(54) LOCAL COOLING ANESTHESIA DEVICE, METHOD OF CONTROLLING LOCAL COOLING ANESTHESIA DEVICE, AND COOLING TEMPERATURE REGULATOR OF LOCAL COOLING ANESTHESIA DEVICE

(71) Applicant: RECENSMEDICAL, INC., Ulsan (KR)

(72) Inventor: Gun Ho Kim, Ulsan (KR)

(73) Assignee: RECENSMEDICAL, INC., Hwaseong-si (KR)

( * ) Notice: Subject to any disclaimer, the term of this patent is extended or adjusted under 35 U.S.C. 154(b) by 38 days.

This patent is subject to a terminal disclaimer.

(21) Appl. No.: 17/455,628

(22) Filed: Nov. 18, 2021

(65) Prior Publication Data

US 2022/0072265 A1 Mar. 10, 2022

Related U.S. Application Data

(63) Continuation of application No. 16/412,296, filed on May 14, 2019, now Pat. No. 11,207,488, which is a
(Continued)

(30) Foreign Application Priority Data

Nov. 15, 2016 (KR) ........................ 10-2016-0151947

(51) Int. Cl.
*A61M 19/00* (2006.01)
*A61B 18/02* (2006.01)
*A61F 7/00* (2006.01)

(52) U.S. Cl.
CPC ......... *A61M 19/00* (2013.01); *A61B 18/0218* (2013.01); *A61F 7/00* (2013.01);
(Continued)

(58) Field of Classification Search
CPC .......... A61M 19/00; A61M 2205/3368; A61M 2205/3606; A61M 2205/366;
(Continued)

(56) References Cited

U.S. PATENT DOCUMENTS

| 2,044,823 A | 6/1936 | Whiteside |
| 4,646,735 A | 3/1987 | Seney |

(Continued)

FOREIGN PATENT DOCUMENTS

| CN | 1093975 A | 10/1994 |
| CN | 2660834 Y | 12/2004 |

(Continued)

OTHER PUBLICATIONS

Chinese First Office Action dated Dec. 22, 2020 for CN 201780083128.0.
(Continued)

*Primary Examiner* — Joseph A Stoklosa
*Assistant Examiner* — Adam J Avigan
(74) *Attorney, Agent, or Firm* — Knobbe, Martens, Olson & Bear, LLP

(57) ABSTRACT

Disclosed is a local cooling anesthesia device for spraying a coolant on a treatment site. The local cooling anesthesia device includes a housing which forms an outward form and from which the coolant is sprayed and a spraying unit installed in the housing to spray the coolant. The device also includes a cooling temperature regulator connected to the spraying unit to apply thermal energy to the sprayed coolant for temperature regulation and a control unit connected to the cooling temperature regulator to control the cooling temperature regulator. The cooling anesthesia device has functions of measuring and regulating the temperature of the coolant, and thus can apply the coolant to the treatment site within a safe temperature range according to the purpose of
(Continued)

treatment, thereby enabling a desired treatment purpose such as local anesthesia to be safely and rapidly accomplished without side effects such as cytostasis.

15 Claims, 6 Drawing Sheets

Related U.S. Application Data continuation of application No. PCT/KR2017/012935, filed on Nov. 15, 2017.

(52) U.S. Cl.
CPC .......... *A61F 2007/0063* (2013.01); *A61F 2007/0064* (2013.01); *A61F 2007/0087* (2013.01); *A61F 2007/0095* (2013.01); *A61M 2205/3368* (2013.01); *A61M 2205/3606* (2013.01); *A61M 2205/366* (2013.01)

(58) Field of Classification Search
CPC .......... A61M 2202/03; A61F 7/00; A61F 2007/0063; A61F 2007/0064; A61F 2007/0087; A61F 7/0085; A61B 18/0218; A61B 18/02; A61B 2018/00791; A61B 2018/00452; A61B 2018/00714; A61B 2018/00642

See application file for complete search history.

(56) References Cited

U.S. PATENT DOCUMENTS

| | | |
|---|---|---|
| 6,099,521 A | 8/2000 | Shadduck |
| 6,141,985 A | 11/2000 | Cluzeau et al. |
| 6,632,219 B1 | 10/2003 | Baranov et al. |
| 6,669,688 B2 | 12/2003 | Svaasand et al. |
| 7,037,326 B2 | 5/2006 | Lee |
| 7,780,656 B2 | 8/2010 | Tankovich |
| 7,963,959 B2 | 6/2011 | Silva et al. |
| 8,083,734 B2 | 12/2011 | Steinfatt et al. |
| D658,775 S | 5/2012 | Jiangminhui |
| 8,177,827 B2 | 5/2012 | Shapiro |
| 8,256,233 B2 | 9/2012 | Boyden et al. |
| 8,409,184 B2 | 4/2013 | Baust et al. |
| 8,652,131 B2 | 2/2014 | Muller et al. |
| 8,672,879 B2 | 3/2014 | Grant et al. |
| 8,747,397 B2 | 6/2014 | Baust et al. |
| 8,758,419 B1 | 6/2014 | Quisenberry et al. |
| 8,788,060 B2 | 7/2014 | Nebrigic et al. |
| 8,858,583 B2 | 10/2014 | Shtram et al. |
| 9,017,318 B2 | 4/2015 | Fourkas et al. |
| 9,039,688 B2 | 5/2015 | Palmer, III et al. |
| 9,066,712 B2 | 6/2015 | Fourkas et al. |
| 9,113,855 B2 | 8/2015 | Burger et al. |
| 9,155,584 B2 | 10/2015 | Fourkas et al. |
| 9,398,975 B2 | 7/2016 | Müller et al. |
| 9,522,031 B2 | 12/2016 | Anderson et al. |
| 9,549,773 B2 | 1/2017 | Anderson et al. |
| 9,642,741 B2 | 5/2017 | Feng et al. |
| 9,801,677 B2 | 10/2017 | Anderson et al. |
| 9,855,166 B2 | 1/2018 | Anderson et al. |
| 9,956,355 B2 | 5/2018 | Besirli et al. |
| 9,974,684 B2 | 5/2018 | Anderson et al. |
| D822,841 S | 7/2018 | Cheng |
| 10,085,881 B2 | 10/2018 | Karnik et al. |
| 10,154,870 B2 | 12/2018 | Ottanelli |
| 10,188,444 B2 | 1/2019 | Fourkas et al. |
| 10,213,244 B2 | 2/2019 | Fourkas et al. |
| 10,322,248 B2 | 6/2019 | Besirli et al. |
| 10,349,997 B1 | 7/2019 | O'Reilly |
| 10,363,080 B2 | 7/2019 | Elkins et al. |
| 10,543,032 B2 | 1/2020 | Babkin et al. |
| 10,993,882 B2 | 5/2021 | Kim |
| 11,154,417 B2 | 10/2021 | Kim |
| 2003/0236561 A1* | 12/2003 | Lennox ............. A61F 7/0085 607/104 |
| 2004/0102768 A1 | 5/2004 | Cluzeau et al. |
| 2004/0111087 A1 | 6/2004 | Stern et al. |
| 2005/0005626 A1 | 1/2005 | McMahon |
| 2005/0059940 A1 | 3/2005 | Weber et al. |
| 2005/0261753 A1 | 11/2005 | Littrup et al. |
| 2006/0106363 A1 | 5/2006 | Aravena et al. |
| 2006/0200117 A1 | 9/2006 | Hermans |
| 2006/0213509 A1 | 9/2006 | Marin et al. |
| 2007/0005048 A1 | 1/2007 | Niedbala et al. |
| 2008/0164296 A1 | 7/2008 | Shelton et al. |
| 2008/0221561 A1 | 9/2008 | Geiger et al. |
| 2009/0005843 A1 | 1/2009 | Smyth |
| 2009/0036846 A1 | 2/2009 | Dacquay et al. |
| 2009/0062751 A1 | 3/2009 | Newman, Jr. |
| 2009/0124972 A1 | 5/2009 | Fischer et al. |
| 2009/0149930 A1* | 6/2009 | Schenck ............. A61B 18/14 607/100 |
| 2009/0163902 A1 | 6/2009 | DeLonzor et al. |
| 2009/0171333 A1 | 7/2009 | Hon |
| 2010/0010480 A1 | 1/2010 | Mehta et al. |
| 2010/0087805 A1 | 4/2010 | Citterio et al. |
| 2010/0192947 A1 | 8/2010 | Mandel et al. |
| 2010/0196343 A1 | 8/2010 | O'Neil et al. |
| 2010/0198207 A1 | 8/2010 | Elkins et al. |
| 2011/0046556 A1 | 2/2011 | Kraft |
| 2011/0072834 A1 | 3/2011 | Ishikura et al. |
| 2011/0098791 A1 | 4/2011 | Kim |
| 2011/0137268 A1 | 6/2011 | Thomason et al. |
| 2011/0152850 A1 | 6/2011 | Niedbala et al. |
| 2011/0177474 A1 | 7/2011 | Jamnia et al. |
| 2011/0224761 A1 | 9/2011 | Manstein |
| 2012/0130458 A1 | 5/2012 | Ryba et al. |
| 2012/0191166 A1 | 7/2012 | Callister et al. |
| 2012/0232549 A1 | 9/2012 | Willyard et al. |
| 2012/0265278 A1 | 10/2012 | Fourkas et al. |
| 2013/0116719 A1 | 5/2013 | Shtram et al. |
| 2013/0184694 A1 | 7/2013 | Fourkas et al. |
| 2013/0218148 A1 | 8/2013 | Burger et al. |
| 2013/0296811 A1* | 11/2013 | Bangera ............. A61B 18/0218 604/290 |
| 2013/0315924 A1 | 11/2013 | Hsu et al. |
| 2014/0012226 A1 | 1/2014 | Hochman |
| 2014/0200511 A1 | 7/2014 | Boyden et al. |
| 2014/0277023 A1 | 9/2014 | Sekino et al. |
| 2014/0303608 A1 | 10/2014 | Taghizadeh |
| 2014/0318153 A1 | 10/2014 | Llercil |
| 2015/0051545 A1 | 2/2015 | Henderson et al. |
| 2015/0122257 A1 | 5/2015 | Winkler et al. |
| 2016/0058488 A1 | 3/2016 | Fourkas et al. |
| 2016/0135864 A1 | 5/2016 | Babkin |
| 2016/0143802 A1 | 5/2016 | Tranfaglia et al. |
| 2016/0183996 A1 | 6/2016 | Burger et al. |
| 2016/0242956 A1 | 8/2016 | Gomez |
| 2016/0262820 A1 | 9/2016 | Allison et al. |
| 2016/0279350 A1 | 9/2016 | Besirli et al. |
| 2017/0014174 A1 | 1/2017 | Levine et al. |
| 2017/0062793 A1 | 3/2017 | Zakharyan et al. |
| 2017/0231816 A1 | 8/2017 | Ryan |
| 2017/0232243 A1 | 8/2017 | Herweijer |
| 2017/0304558 A1 | 10/2017 | Besirli et al. |
| 2017/0354451 A1* | 12/2017 | Marin ............. A61B 18/0218 |
| 2018/0028250 A1* | 2/2018 | O'Connor ............. A61F 2/958 |
| 2018/0116705 A1 | 5/2018 | Lee et al. |
| 2018/0235805 A1 | 8/2018 | Burger et al. |
| 2018/0310979 A1 | 11/2018 | Peled et al. |
| 2019/0000524 A1 | 1/2019 | Rosen et al. |
| 2019/0015146 A1 | 1/2019 | DuBois et al. |
| 2019/0038459 A1 | 2/2019 | Karnik et al. |
| 2019/0175394 A1 | 6/2019 | Kim |
| 2019/0175395 A1 | 6/2019 | Kim |
| 2019/0175396 A1 | 6/2019 | Kim |
| 2019/0239938 A1 | 8/2019 | Kazic et al. |
| 2019/0254866 A1* | 8/2019 | Whiteley ............. A61M 19/00 |
| 2019/0290881 A1 | 9/2019 | Kim |
| 2020/0054483 A1 | 2/2020 | Kim |
| 2020/0100934 A1 | 4/2020 | Ariano et al. |

(56) References Cited

U.S. PATENT DOCUMENTS

| | | |
|---|---|---|
| 2020/0309436 A1 | 10/2020 | Kim |
| 2021/0007882 A1 | 1/2021 | Kim |
| 2021/0007883 A1 | 1/2021 | Kim |
| 2021/0220164 A1 | 7/2021 | Kim |
| 2021/0290430 A1 | 9/2021 | Kim |
| 2021/0338478 A1 | 11/2021 | Kim |

FOREIGN PATENT DOCUMENTS

| | | |
|---|---|---|
| CN | 1869551 A | 5/2006 |
| CN | 2861867 Y | 1/2007 |
| CN | 201233093 Y | 5/2009 |
| CN | 101678169 A | 3/2010 |
| CN | 102026597 A | 4/2011 |
| CN | 201876179 U | 6/2011 |
| CN | 102202709 A | 9/2011 |
| CN | 102755190 A | 10/2012 |
| CN | 102892369 A | 1/2013 |
| DE | 196 45 299 A1 | 4/1998 |
| EP | 1 030 611 B1 | 9/2004 |
| EP | 1 892 484 A1 | 2/2008 |
| EP | 1 401 347 B1 | 8/2011 |
| EP | 2 010 087 B1 | 11/2014 |
| EP | 2 910 276 A1 | 8/2015 |
| EP | 2 759 272 B1 | 11/2018 |
| FR | 777286 A | 2/1935 |
| FR | 1510727 A | 1/1968 |
| FR | 2579888 A1 | 10/1986 |
| FR | 2795629 A1 | 1/2001 |
| GB | 717850 A | 11/1954 |
| JP | S57-20265 A | 2/1982 |
| JP | 04-092663 A | 3/1992 |
| JP | 06-086818 A | 3/1994 |
| JP | 10-230435 A | 9/1998 |
| JP | H11 342149 A | 12/1999 |
| JP | 2002-505155 A | 2/2002 |
| JP | 4049358 B2 | 2/2002 |
| JP | 2004-515270 A | 5/2004 |
| JP | 2005-080832 A | 3/2005 |
| JP | 2008-212638 A | 9/2008 |
| JP | 2008-545462 A | 12/2008 |
| JP | 2009-034273 A | 2/2009 |
| JP | 2009-056320 A | 3/2009 |
| JP | 2011-077314 A | 4/2011 |
| JP | 2012-143279 A | 8/2012 |
| JP | 2013-142410 A | 7/2013 |
| JP | 2014-198238 A | 10/2014 |
| JP | 2015-510802 A | 4/2015 |
| JP | 2017-113635 A | 6/2017 |
| KR | 20-1998-0005117 U | 3/1998 |
| KR | 10-0200669 B1 | 3/1999 |
| KR | 10-2003-0068633 A | 8/2003 |
| KR | 10-2004-0093706 A | 11/2004 |
| KR | 10-0786539 B1 | 12/2007 |
| KR | 10-0790758 B1 | 12/2007 |
| KR | 10-2008-0045022 A | 5/2008 |
| KR | 10-0851274 B1 | 8/2008 |
| KR | 10-2010-0041207 A | 4/2010 |
| KR | 10-2010-0060222 A | 6/2010 |
| KR | 10-2010-0135863 A | 12/2010 |
| KR | 10-1053835 B1 | 8/2011 |
| KR | 10-2011-0119640 A | 11/2011 |
| KR | 10-2012-0115703 A | 10/2012 |
| KR | 10-1208655 B1 | 11/2012 |
| KR | 10-2013-0087770 A | 8/2013 |
| KR | 10-1366126 B1 | 2/2014 |
| KR | 10-1386137 B1 | 4/2014 |
| KR | 10-2014-0052667 A | 5/2014 |
| KR | 10-2014-0069431 A | 6/2014 |
| KR | 10-2015-0030264 A | 3/2015 |
| KR | 10-2015-0062492 A | 6/2015 |
| KR | 10-2016-0033282 A | 3/2016 |
| KR | 10-2016-0048425 A | 5/2016 |
| KR | 10-1650155 B1 | 8/2016 |
| KR | 10-2016-0146337 A | 12/2016 |
| KR | 10-1707659 B1 | 2/2017 |
| KR | 10-1719459 B1 | 3/2017 |
| KR | 10-2017-0041776 A | 4/2017 |
| KR | 10-2017-0083399 A | 7/2017 |
| KR | 10-2017-0089842 A | 8/2017 |
| KR | 10-1813652 B1 | 8/2017 |
| KR | 10-2017-0130470 A | 11/2017 |
| KR | 10-1819204 B1 | 1/2018 |
| KR | 10-2018-0054247 A | 5/2018 |
| KR | 10-1840346 B1 | 5/2018 |
| KR | 10-1862127 B1 | 5/2018 |
| KR | 10-2018-0109828 A | 10/2018 |
| KR | 10-1936890 B1 | 1/2019 |
| KR | 10-2019-0074150 A | 6/2019 |
| WO | WO 2016/010428 A1 | 1/2016 |
| WO | WO 2016/113305 A1 | 7/2016 |
| WO | WO 2016/154399 A1 | 9/2016 |
| WO | WO 2018/231868 A1 | 12/2018 |

OTHER PUBLICATIONS

European (EUIPO) Examination Report dated Jan. 11, 2021 for 008309504-003.
European (EUIPO) Examination Report dated Feb. 5, 2021 for 008309504-003.
International Search Report dated Jun. 4, 2018 for PCT/KR2017/012935.
International Search Report dated Jul. 6, 2018 for PCT/KR2018/003773.
International Search Report dated Aug. 8, 2018 for PCT/KR2017/013901.
|International Search Report dated May 30, 2019 for PCT/KR2018/016491.
International Search Report and Written Opinion dated Aug. 14, 2019 for PCT/KR2019/005105.
International Search Report and Written Opinion dated Nov. 15, 2019 for PCT/KR2019/009411.
International Search Report dated Mar. 27, 2020, for PCT/KR2019/017328.
International Search Report dated Mar. 4, 2021, for PCT/KR2020/012886.
International Written Opinion dated Mar. 4, 2021, for PCT/KR2020/012886.
Korean Notice of Allowance dated Jun. 30, 2018 for KR 10-2016-0151947.
Korean Office Action dated Oct. 22, 2018 for KR 10-2017-0162715.
Korean Notice of Allowance dated Aug. 29, 2019 for KR 10-2017-0162715.
Korean Office Action dated Oct. 22, 2018 for KR 10-2017-0162716.
Korean Notice of Allowance dated Jul. 29, 2019 for KR 10-2017-0162716.
Korean Office Action dated Jul. 29, 2019 for KR 10-2017-0162717.
Korean Final Office Action dated Jan. 17, 2020 for KR 10-2017-0162717 with Translation.
Korean Office Action dated Nov. 26, 2019 for KR 10-2018-0049108—w/ Trans.
Korean Final Office Action dated May 10, 2020, for KR 10-2018-0049109 with Translation.
Korean Office Action dated Nov. 27, 2019 for KR 10-2018-0049109—w/ Trans.
Korean Notice of Allowance dated Jun. 24, 2020 for KR 10-2018-0049109—w/ Trans.
Korean Office Action dated Dec. 6, 2019 for KR 10-2018-0049110—w/ Trans.
Korean Final Office Action dated May 10, 2020 for KR 10-2018-0049110—w/ Trans.
Korean Notice of Allowance dated Jun. 22, 2020 for KR 10-2018-0049110—w/ Trans.
Korean Office Action dated Dec. 9, 2019 for KR 10-2018-0049115—w/ Trans.
Korean Office Action dated May 10, 2020 for KR 10-2018-0049115, with Eng. Translation.
Korean Notice of Allowance dated Jul. 21, 2020 for KR 10-2018-0049115—w/ Trans.

(56) References Cited

OTHER PUBLICATIONS

Korean Office Action dated Dec. 10, 2019 for KR 10-2018-0049117—w/ Trans.
Korean Notice of Allowance dated May 10, 2020 for KR 10-2018-0049117.
Korean Office Action dated Oct. 8, 2019 for KR 10-2018-0052601.
Korean Second Office Action, with translation, dated Oct. 28, 2019 for KR 10-2018-0052601.
Korean Notice of Allowance dated Apr. 2, 2020 for KR 10-2018-0052601 with Eng. Translation.
Korean Office Action dated Oct. 22, 2018, for KR 10-2018-0117138.
Office Action dated Oct. 2, 2019 for U.S. Appl. No. 15/828,449.
Office Action dated May 15, 2020 for U.S. Appl. No. 15/828,449.
Office Action dated Sep. 13, 2019 for U.S. Appl. No. 16/412,296.
Final Office Action dated Jan. 31, 2020 for U.S. Appl. No. 16/412,296.
Office Action dated Jun. 26, 2020 for U.S. Appl. No. 16/412,296.
Final Office Action dated Oct. 28, 2020 for U.S. Appl. No. 16/412,296.
Notice of Allowance dated Aug. 20, 2021 for U.S. Appl. No. 16/412,296.
Office Action Dated Dec. 24, 2020 for US App. No. 17,036,269.
Office Action dated Dec. 8, 2020 for U.S. Appl. No. 17/036,311.
Notice of Allowance dated Feb. 22, 2021 for U.S. Appl. No. 17/036,311.
Office Action dated Nov. 5, 2020 for U.S. Appl. No. 29/701,630.
Notice of Allowance dated Feb. 3, 2021 for U.S. Appl. No. 29/701,630.
Office Action dated Nov. 5, 2020 for U.S. Appl. No. 29/701,631.
Notice of Allowance dated Feb. 3, 2021 for U.S. Appl. No. 29/701,631.
Smith et al., "Ice Anesthesia for Injection of Dermal Fillers," The American Society for Dermatologic Surgery Inc., Dermatol. Surg 2010;36:812-814, 2010.
Sarifakioglu, et al., "Evaluating the Effects of Ice Application on the Pain Felt During Botulinum Toxin Type-A Injections," Annals of Plastic Surgery, vol. 53, No. 6, Dec. 2004.
Office Action Dated Sep. 10, 2021 for U.S. Appl. No. 16/903,186.
Final Office Action Dated Apr. 13, 2021 for US App. No. 17,036,269.
Notice of Allowance dated Mar. 26, 2021 for U.S. Appl. No. 17/036,311.
Office Action dated Sep. 1, 2021 for U.S. Appl. No. 17/335,330.
Notice of Allowance dated Apr. 13, 2021 for U.S. Appl. No. 29/701,630.
Corrected Notice of Allowance dated Apr. 20, 2021 for U.S. Appl. No. 29/701,630.
Notice of Allowance dated Apr. 13, 2021 for U.S. Appl. No. 29/701,631.
Corrected Notice of Allowance dated May 5, 2021 for U.S. Appl. No. 29/701,631.
Chinese Office Action dated Dec. 22, 2020 with Eng. Translation for CN 10-2017-0083128.
Chinese Office Action dated Dec. 22, 2020 with Eng. Translation for CN20170083128.0.
Chinese Notice of Allowance, with Eng. Translation dated Dec. 20, 2022 for CN 201780083128.0.
Korean Office Action dated Dec. 22, 2020 with Eng. Translation for KR 10-2017-0083128.
Korean Office Action dated Dec. 20, 2021 with Eng. Translation for KR 10-2018-0117137.
Korean Office Action dated Jun. 2, 2022 with Eng. Translation for KR 10-2018-0117137.
Korean Notice of Allowance dated Dec. 1, 2022 with Eng. Translation for KR 10-2018-0117137.

\* cited by examiner

LOCAL COOLING ANESTHESIA DEVICE, METHOD OF CONTROLLING LOCAL COOLING ANESTHESIA DEVICE, AND COOLING TEMPERATURE REGULATOR OF LOCAL COOLING ANESTHESIA DEVICE

CROSS-REFERENCE TO RELATED APPLICATIONS

This application is a continuation of U.S. patent application Ser. No. 16/412,296, filed on May 14, 2019, which is a continuation and claims the benefit under 35 U.S.C. §§ 120 and 365 of PCT Application No. PCT/KR2017/012935, filed on Nov. 15, 2017, which claims priority to Korean Patent Application No. 10-2016-0151947 filed on Nov. 15, 2016, each of which is hereby incorporated by reference in its entirety.

TECHNICAL FIELD

The described technology generally relates to a local cooling anesthesia device, control methods of the local cooling anesthesia device, and an adjuster of cooling temperature of the local cooling anesthesia device.

RELATED TECHNOLOGY

In general, unlike use of medication such as lidocaine and the like, a device used in cooling anesthesia may render a local area to an anesthetized state in a short time and is useful for local anesthesia necessary in a variety of medical procedures.

In the case of an anesthetic such as lidocaine and the like, there are limitations such as the long onset time of anesthetics required to reach a pain receptor through an outer skin layer and a limited effect of anesthesia without direct hypodermic injection.

For example, laser treatment used for various therapies, beauty treatment, and the like can accompany with death of a large quantity of cells, and hence cause severe pain, making a great need for effective local anesthesia. A method of anesthesia using an anesthetic such as lidocaine and the like used as a standard method of anesthesia before laser treatment typically requires 30 minutes or more for onset of anesthesia, which lengthens both patient waiting time and workflow at clinics. Also, since an effect thereof can be largely limited without direct injection, patient satisfaction can be poor, and particularly, laser treatment for children has great practical difficulties.

In contrast, a cooling anesthesia device can not only provide a significantly quicker anesthetic effect in comparison to an anesthetic, but also, as the cooling device uses low temperatures to induce anesthesia, can protect the peripheral cells from thermal burn in laser treatment and thereby minimize a risk of erythema, purpura, crusting, and the like, which are general side effects of laser treatment. In addition to laser treatment, a rapid cooling anesthesia device may be useful in a variety of medical procedures such as painless blood collection, painless injection, simple resection, and the like.

In a method of anesthesia using cooled air, due to low heat capacity of the air, it is difficult to decrease a temperature of a treatment area to a degree at which an anesthetic effect appears. Cryogenic coolants such as liquid nitrogen, $CO_2$, and the like provide a strong and rapid cooling effect due to its efficient heat absorption process with a large latent heat during a phase change of the coolant. However, since a predetermined evaporation point or a liquefaction point of the cryogenic coolant is typically lower than the temperature of necrosis of the target cells, the aforementioned cryogenic cooling is generally used in a procedure which requires cell destruction, such as destruction of cancel cells and the like. In the case of cooling anesthesia using cryogenic coolant such as liquid nitrogen, $CO_2$, or the like, absence of precise control of the temperature of the cryogenic coolant may lead to a temperature at the target area below a safe temperature range and cause destruction of healthy normal cells.

Although a spray amount or a spray time of the coolant may be adjusted to prevent excessive cooling, in this case, a temperature of the coolant itself, which is applied to the treatment area, remains at a dangerous temperature, which causes cytoclasis, such that it is difficult to reduce a risk caused by excessive cooling. Particularly, when the coolant is sprayed for an adequate time for cooling skin and a sensory nerve plexus, a temperature of epidermal cells is excessively lowered such that additional pain is caused due to cytoclasis. When the coolant is applied for a short time in order to prevent destruction of skin cells, it is impossible to adequately cool the sensory nerve plexus such that an anesthetic effect can be insignificant.

SUMMARY

One aspect is a local cooling anesthesia device, which rapidly and accurately adjusts a temperature of a coolant provided to a treatment area, measures the temperature of the coolant and the target area, and therefore applies the coolant for an adequate time enough to induce an anesthesia effect without the risk of cytoclasis and the like, a method of controlling the local cooling anesthesia device, and a cooling temperature adjuster of the local cooling anesthesia device.

Another aspect is a local cooling anesthesia device, which performs cooling anesthesia on a treatment area by spraying a coolant on the treatment area. Here, the local cooling anesthesia device includes a housing which forms an exterior and from which the coolant is sprayed, a sprayer installed in the housing to spray the coolant, a cooling temperature adjuster which is connected to the sprayer and applies heat energy to the coolant being sprayed to adjust a temperature, and a controller connected to the cooling temperature adjuster to control the cooling temperature adjuster.

The local cooling anesthesia device may further include a supplier installed in the housing to supply the coolant to the sprayer.

The supplier may further include a compressor which compresses the coolant to provide a supply pressure of the coolant.

The coolant may be $CO_2$, liquid nitrogen, or air.

The coolant may reduce its temperature through an endothermic reaction in the air.

The local cooling anesthesia device may further include a power supply installed in the housing to supply power to an inside of the housing.

The sprayer may include a nozzle installed on a transfer line, through which the coolant is transferred, to spray the coolant and a valve installed on the transfer line to adjust an amount of the coolant supplied through the transfer line.

The sprayer may include a nozzle, through which the coolant is sprayed, and a valve installed on a transfer line of the coolant transferred to the nozzle to open or close the transfer line.

The controller may include a temperature measurer for detecting a temperature of the treatment area and a temperature sensor installed in the cooling temperature adjuster to detect a temperature of the cooling temperature adjuster, and may have a structure in which equations for controlling a temperature of a heat source installed at the cooling temperature adjuster are embedded, which can calculate the proper heat energy applied to the cooling temperature adjuster or the proper spray amount of the sprayer and adjusted the heat energy or the spray amount based on the difference between the target cooling temperature and the measured temperature at the target area.

The temperature measurer may be disposed while being spaced apart from a position of spraying the coolant on the treatment area.

The controller may further include an input portion for inputting a setting value and a display portion for externally displaying a signal applied to the controller.

The display portion may include a display for displaying information and a warning light for displaying a visual warning or an alarm for an aural warning.

The cooling temperature adjuster may include a heat source for heating the coolant and a heat exchanger for transferring heat of the heat source to the coolant.

The local cooling anesthesia device may further include a cooling structure which is installed at a front end of the housing, connected to and cooled by the heat exchanger of the cooling temperature adjuster, and cools the treatment area through surface contact with the treatment area.

Another aspect is a cooling temperature adjuster of a local cooling anesthesia device spraying a coolant on a treatment area to perform cooling anesthesia thereon, which is installed in the local cooling anesthesia device to adjust a temperature of the coolant sprayed on the treatment area. Here, the cooling temperature adjuster includes a heat source for heating the coolant and a heat exchanger for transferring heat of the heat source to the coolant.

The cooling temperature adjuster may include a structure, of which heat is exchanged with the coolant, and quickly approaches the temperature of the coolant to measure the temperature of the coolant through the cooling temperature adjuster.

The heat exchanger may include a heating plate, in which the heat source is installed, and a plurality of heat dissipation fins which are installed on the heating plate and come into contact with the coolant.

The plurality of heat dissipation fins may have a plate shape, which protrudes from the heating plate and extends longitudinally in the direction of the coolant flow, and may be arranged with spatial gaps to increase a contact area of the heat dissipation fins with the coolant.

The cooling temperature adjuster may have a structure in which the heating plate of the heat exchanger has a hollow and cylindrical shape, the heat dissipation fins are installed to be arranged along an outer circumferential surface of the heating plate such that heat of the coolant is exchanged with that of the heat dissipation fins while the coolant passes outside the heating plate, and the heat source is installed to be inserted into a center of the heating plate.

The cooling temperature adjuster may have a structure in which the heating plate of the heat exchanger has a hollow polygonal prism shape, the heat dissipation fins are installed to be arranged on an inner circumferential surface of the heating plate such that heat of the coolant is exchanged with that of the heat dissipation fins while the coolant passes through an inside of the heating plate, and the heat source is installed on at least one surface of the heating plate.

The heat exchanger may have a structure in which a diameter gradually decreases toward an end along a coolant spray direction.

The heat source may be one of an electric heater, a thermoelectric element, and a structure which applies heat by emitting light or electromagnetic waves.

The heat exchanger may include a metal material having high thermal conductivity.

The cooling temperature adjuster may have a structure in which a sealant for heat insulation is further installed on an outside thereof to prevent heat transfer with the outside.

Another aspect is a method of controlling a local cooling anesthesia device, which includes a sprayer for spraying a coolant on a treatment area, a cooling temperature adjuster for adjusting a temperature of the coolant, and a controller connected to the cooling temperature adjuster to control the cooling temperature adjuster and perform cooling anesthesia on the treatment area by spraying the coolant thereon. Here, the method includes setting a target cooling temperature for the treatment area, cooling the treatment area by spraying the coolant thereon, detecting a real temperature of the treatment area, comparing the detected real temperature value with the target cooling temperature, and controlling a temperature of the coolant by adjusting a heat source of the cooling temperature adjuster or a coolant spray amount such that the real temperature value reaches the target cooling temperature.

The setting of the target cooling temperature may further include setting the coolant spray amount.

The controlling of the temperature may include comparing the detected real temperature value with the target cooling temperature and calculating whether an absolute value of a difference between the real temperature value and the target cooling temperature is smaller than a preset arbitrary alpha value α, a primary calculation operation of controlling the temperature of the coolant by controlling a heat source of the cooling temperature adjuster according to precise cooling control when the absolute value of the difference between the real temperature value and the target cooling temperature is smaller than the alpha value, and a secondary calculation operation of controlling the temperature of the coolant by controlling the heat source of the cooling temperature adjuster according to quick cooling control when the absolute value of the difference between the real temperature value and the target cooling temperature is greater than or equal to the alpha value.

In the controlling of the temperature, the primary calculation operation may be performed through a primary equation 1 for precise cooling control and the secondary calculation operation is performed through a secondary equation 2 for quick cooling control, $$P(t) = C_{p,1}\text{error}(t) + C_{i,1}\int_0^t \text{error}(t)dt + C_{d,1}\frac{d(\text{erroe}(t))}{dt} \quad \text{Primary Equation (1)}$$

$$P(t) = C_{p,2}\text{error}(t) + C_{i,2}\int_0^t \text{error}(t)dt + C_{d,2}\frac{d(\text{erroe}(t))}{dt} \quad \text{Secondary Equation (2)}$$

Here, P(t) is a digital or analog type output value output at a certain time t from the controller, error (t) is a difference between a temperature measured at the time t and a target cooling temperature. Cp, Ci, and Cd are proportional (P), integral (I), and differential (D) constants, which are used in proportional integral differential (PID) control, respectively.

Constants of the primary equation 1 and the secondary equation 2 have different values such that a value of P(t) that is a value obtained by applying the secondary equation 2 may be greater than a value of P(t) obtained by applying the primary equation 1.

The controlling of the temperature may further include calculating whether an absolute value of the difference between the real temperature value, which is detected after the cooling temperature adjuster is driven, and the target cooling temperature is preset and is smaller than a preset arbitrary beta value β, which is smaller than the alpha value α, by comparing the real temperature value with the target cooling temperature, driving a timer when the absolute value of the difference between the real temperature value and the target cooling temperature is smaller than the beta value, and completing cooling anesthesia after a setting time of the timer has passed.

In the controlling of the temperature, temperature control may be performed including three or more stages of calculation.

In the controlling of the temperature, when high-speed cooling is necessary in an early stage, the constant of the secondary equation 2 may be set such that power applied to the heat source of the cooling temperature adjuster becomes zero.

In the controlling of the temperature, when low-speed cooling is necessary in an early stage, the constant of the secondary equation 2 may set a power value applied to the heat source of the cooling temperature adjuster such that the temperature of the coolant changes at a speed of 1° C./sec.

The controlling of the temperature may further include decreasing a temperature of the cooling temperature adjuster in advance by spraying the coolant in advance when high-speed cooling is necessary in an early stage.

According to at least one of the disclosed embodiments, a coolant may be applied to a treatment area at a temperature within a safe range in accordance with a treatment purpose by having a function of measuring and adjusting a temperature of the coolant. Accordingly, a desirable treatment purpose such as local anesthesia and the like may be safely and quickly performed without side effects such as cytoclasis and the like.

Also, since the coolant may be applied for a long time without destruction of epidermal cells, skin and a sensory nerve plexus may be safely cooled through an adequate application time. Accordingly, a strong local anesthesia effect may be obtained.

DETAILED DESCRIPTION

The technical terms used hereafter are merely for describing a particular embodiment and are not intended to limit the present invention. Singular forms used herein, unless clearly defined otherwise, include plural forms. The meaning of "comprising" specifies a particular property, area, integer, step, operation, element, and/or component and does not exclude presence or addition of another particular property, area, integer, step, operation, element, component, and/or group thereof.

Hereinafter, embodiments will be described with reference to the attached drawings such as to be easily performed by one of ordinary skill in the art. As understood by one of ordinary skill in the art, the following embodiments may be modified into a variety of forms without departing from the concept and range of the present invention. The present invention may be embodied in a variety of different forms and is not limited to the embodiment disclosed herein.

Hereafter, a device which has a treatment purpose of performing local anesthesia that is applicable to laser treatment will be described as an example. However, a local cooling anesthesia device is not limited to local anesthesia in treatment purposes and is applicable to all various cases of treatment such as cancer treatment, of which a treatment purpose is cytoclasis as necessary.

Figure 1:
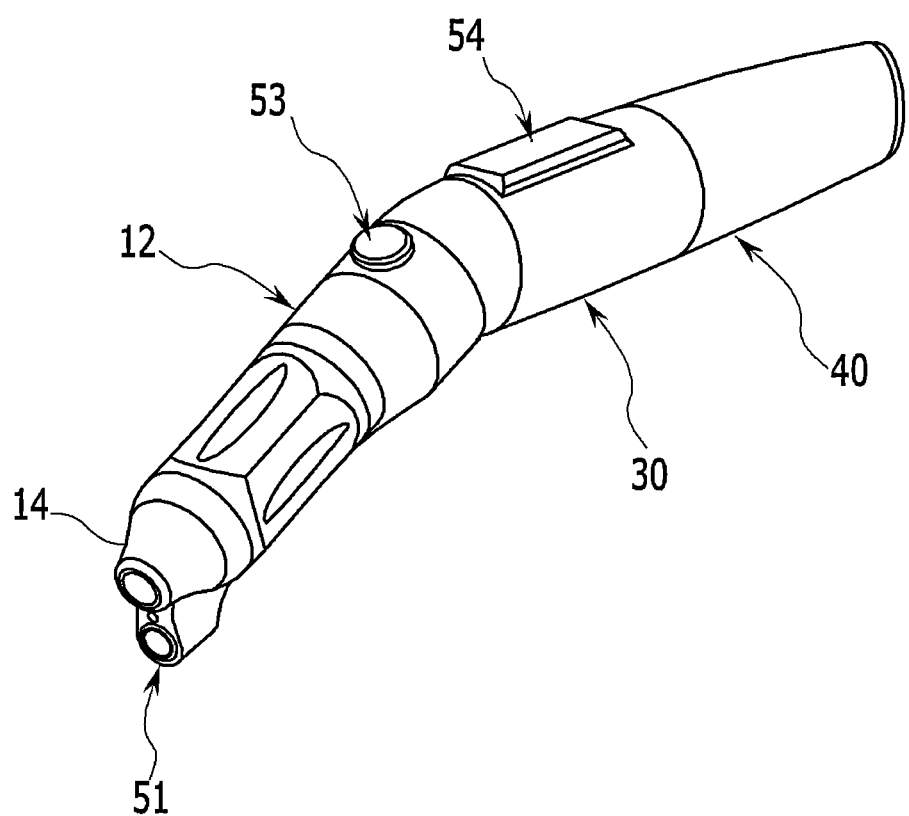
FIG. 1 is a schematic perspective view illustrating a local cooling anesthesia device including a cooling temperature adjuster according to an embodiment.
Figure 2:
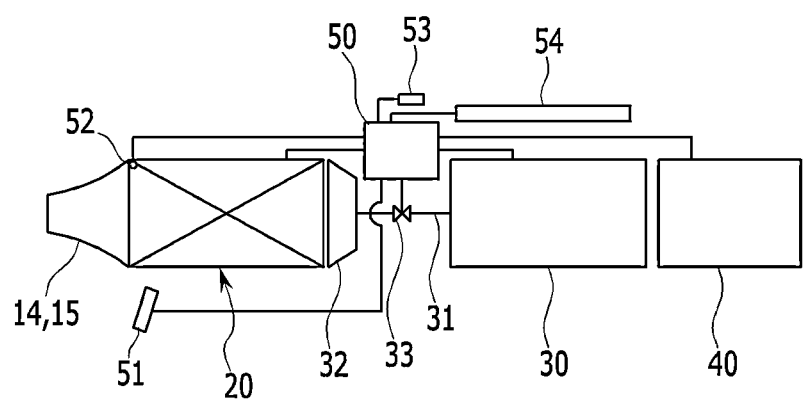
FIG. 2 is a schematic diagram illustrating components of the local cooling anesthesia device according to the embodiment.
Figure 3:
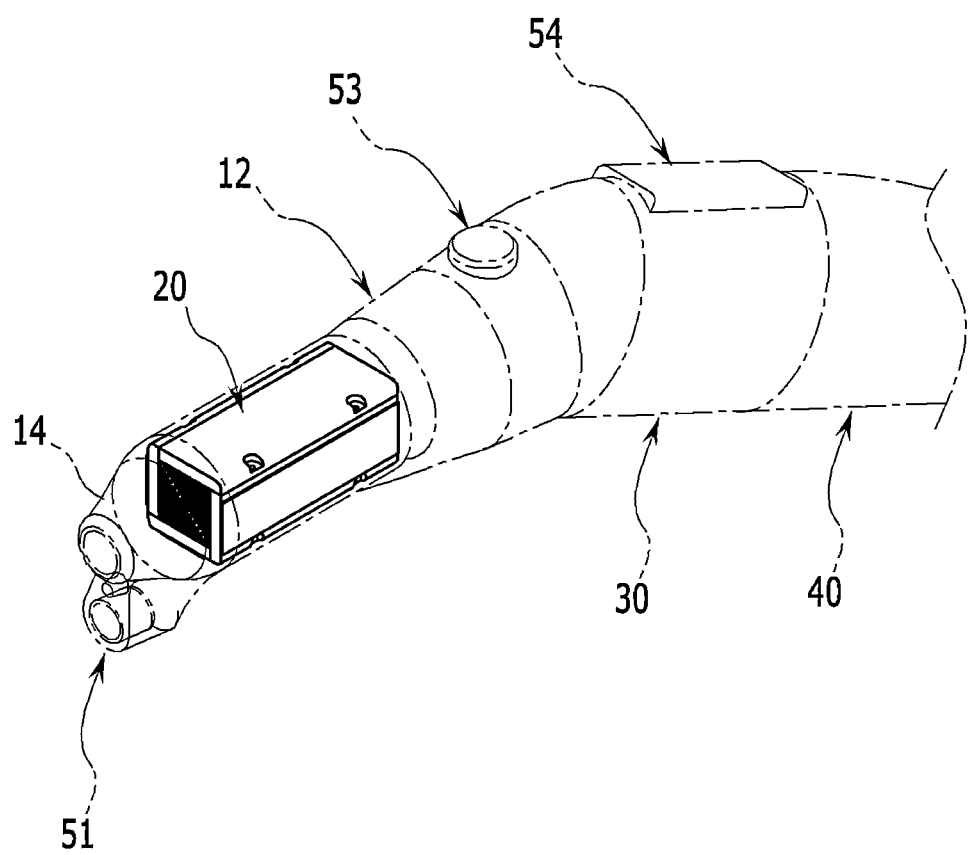
FIG. 3 is a schematic diagram illustrating a state in which the cooling temperature adjuster is installed in the local cooling anesthesia device according to the embodiment.

FIGS. 1 and 2 illustrate components of a local cooling anesthesia device including a cooling temperature adjuster according to an embodiment, and FIG. 3 schematically illustrates a state in which the cooling temperature adjuster according to the embodiment is installed.

A local cooling anesthesia device 10 according to an embodiment includes a housing 12, which forms an exterior, and a sprayer, a cooling temperature adjuster 20, a controller 50, a supplier 30, and a power supply 40, which are installed in the housing 12.

In the embodiment, both the supplier 30 for supplying a coolant and the power supply 40 for providing power are included in the housing 12 so as to form a portable device in which the housing 12 itself may be driven independently. Unlike this structure, for high power driving, the supplier 30 or the power supply 40 may be separately disposed outside the housing 12 and a coolant or power may be supplied from the outside to the inside of the housing 12 through additional lines.

As shown in FIG. 1, the housing 12 may protect internal components by forming the exterior of the device and include an insulating material to prevent the cold of the coolant or heat energy of the cooling temperature adjuster 20 from being transferred to the outside. The housing 12 may have an ergonomic shape so as to be easily gripped by a user. Although an external shape of the housing 12 is shown in FIG. 1, the housing 12 is not limited thereto and may be modified into a variety of shapes to be easily usable by a user.

A spray hole 14 for spraying the coolant on a treatment area is formed at a proximal end of the housing 12. A temperature measurer 51 for measuring a temperature of the treatment area is installed while spaced a certain distance apart and below the spray hole 14. Also, an input portion 53 and a display portion 54 for controlling and operating the device are installed on a certain side of the housing 12. The temperature measurer, the input portion, and the display portion will be described below in detail.

The spray hole 14 is smoothly connected to the cooling temperature adjuster 20 disposed inside the housing 12. Accordingly, the coolant, of which temperature is adjusted while passing through the cooling temperature adjuster 20, may be easily sprayed through the spray hole 14. The spray hole 14 may be further combined with a lighting portion to emit light toward the treatment area. For example, light emitting diodes (LEDs), which emit light, are installed along an outside of the spray hole 14 such that light of the LEDs may be emitted toward the treatment area.

The supplier 30 may be a pressure container which is installed in the housing 12 and filled with a coolant. The pressure container may be filled with a compressed coolant. The supplier 30 may further include a compressor for compressing a coolant to provide a supply pressure of the coolant. The pressure container that is the supplier 30 may be filled with the coolant at high pressure through the compressor.

As the coolant, a variety of materials such as liquid nitrogen, CO2, low-temperature cooled air, and the like may be used. Also, the coolant may be a material capable of lowering a temperature of a treatment area through endothermic reaction in the air.

Hereafter, in the embodiment, a case of using CO2 as the coolant will be described as an example. The pressure container is a container filled with CO2 at a high pressure and is connected to the sprayer and supplies high-pressure CO2 to the sprayer. For example, the pressure container may withstand a pressure of 600 kPa and store 50 g of CO2.

The supplier may include a high-capacity pressure container of 1 kg or more which stores CO2 and which may be disposed outside the housing. In the case of such a structure, CO2 may be supplied from an external pressure container to the sprayer through a long tube.

The sprayer includes a nozzle 32 installed on a transfer line 31, through which a coolant is transferred, to spray the coolant and a valve 33 installed on the transfer line 31 to adjust an amount of the coolant supplied through the transfer line 31.

The transfer line 31 is installed to be connected to the supplier 30. CO2 transferred along the transfer line 31 is sprayed through the nozzle 32 installed on a front end of the transfer line 31. In the embodiment, the nozzle 32 has a hole about 500 μm in diameter and jets a high pressure CO2 coolant to the outside thereof. The valve 33 is controlled and driven according to a signal of the controller 50 and adjusts the amount of the coolant supplied through the transfer line 31. A spray amount of the coolant sprayed through the nozzle 32 to the outside is adjusted by driving of the valve 33.

The power supply 40 is for supplying power necessary for operating components in the housing 12 and, for example, may be a repeatedly-usable secondary battery such as a lithium-ion battery or a replaceable primary battery. The power supply 40 may be detachably installed at the front end of the housing 12.

The cooling temperature adjuster 20 adjusts a temperature of a coolant sprayed on a treatment area by applying heat energy to the coolant sprayed through the nozzle 32 of the sprayer. The cooling temperature adjuster 20 is disposed at the front end of the housing 12, that is, on a coolant movement path between the nozzle 32 of the sprayer and the spray hole 14 at the front end of the housing 12 and exchanges heat with the coolant sprayed from the nozzle 32 to the spray hole 14. The nozzle 32 and the cooling temperature adjuster 20 may be joined to each other using a joining method having high heat transfer. For example, the nozzle 32 and the cooling temperature adjuster 20 may be joined using a medium of a thermal paste.

The cooling temperature adjuster 20 includes a heat source 21 for heating a coolant and a heat exchanger for transferring heat of the heat source 21 to the coolant. The heat exchanger is disposed lengthwise in the housing 12 along a coolant spray direction. To further maximize efficiency in heat exchange between the heat source 21 and the coolant, the heat exchanger includes a heating plate 22, in which the heat source 21 is installed, and a plurality of heat dissipation fins 23 which are installed to the heating plate 22 and contact with the coolant.

The heat exchanger may include a metal material having a high thermal conductivity. The heating plate and the heat dissipation fins 23 may be integrally formed. For example, the heat exchanger may be formed of an aluminum or copper material.

Heat exchange with a coolant is performed through the heat dissipation fins 23. The plurality of heat dissipation fins 23 have a structure of protruding from the heating plate 22, having a plate shape extending lengthwise along a coolant spray direction, and being arranged at intervals to increase a contact area with the coolant. Accordingly, the contact area with the coolant is further increased by the heat dissipation fins 23 so as to maximize heat transfer efficiency.

The heat source 21 may be an electric heater, a thermoelectric element, or a structure of applying heat by emitting light or electromagnetic waves such as infrared rays or microwaves, and the like. In the embodiment, the heat source 21 may have a maximum output of 0.1 to 10 W.

Also, the device may include a discrete cooling structure, which comes into contact with and cools the treatment area, and may spray a coolant not directly on a treatment area, which has passed through the heat exchanger of the cooling temperature adjuster 20.

For example, in the case of an object to be treated, such as an ocular surface and the like, a method of spraying a coolant directly on a treatment area to cool the treatment area may be inadequate. Accordingly, in the case of the object to be treated such as the ocular surface and the like, instead of spraying the coolant, which has passed through the cooling temperature adjuster 20, directly on the treatment area to adjust a temperature thereof, a discrete structure is installed with the cooling temperature adjuster such that the cooling temperature adjuster may adjust a temperature of the discrete structure and the discrete structure may come in to direct contact with the treatment area and reduce a temperature of the treatment area.

To this end, a discrete cooling structure 15, which is connected to the heat exchanger of the cooling temperature adjuster 20 and comes into contact with a treatment area, may be installed at the front end of the housing. The cooling structure 15 may be understood as a structure of blocking plate with a certain area, which has a surface of contacting a treatment area. For example, the cooling structure 15 may be installed at the front end of the housing instead of the spray hole, which sprays a coolant, or may be additionally installed at the spray hole.

The cooling structure 15 blocks the coolant sprayed through the front end of the housing and comes into contact with a treatment area to cool the treatment area. The heat exchanger of the cooling temperature adjuster 20 may be connected to the cooling structure installed at the front end of the housing and adjust a temperature of the cooling structure 15 by applying a coolant, which has passed through the heat exchanger, to the cooling structure.

The cooling structure 15 is cooled by the coolant, which is sprayed and passed through the heat exchanger of the cooling temperature adjuster, and contacts a treatment area to transfer the coolness of the coolant thereto. Accordingly, the coolant is not sprayed directly on the treatment area, and cooling is performed by the cooling structure.

In addition to the above structure, the cooling temperature adjuster 20 may have a structure in which a front end of the heat exchanger is blocked to prevent a coolant from being sprayed and may protrude from the front end of the housing 12. In the case of the structure, a front end of the cooling temperature adjuster 20 may come into direct contact with a treatment area and reduce a temperature of the treatment area.

Also, the heat exchanger may protrude from the front end of the housing 12 to a spray hole directly. In the case of such a structure, the front end of the heat exchanger may come into direct contact with a treatment area to reduce a temperature of the treatment area.

Figure 4:
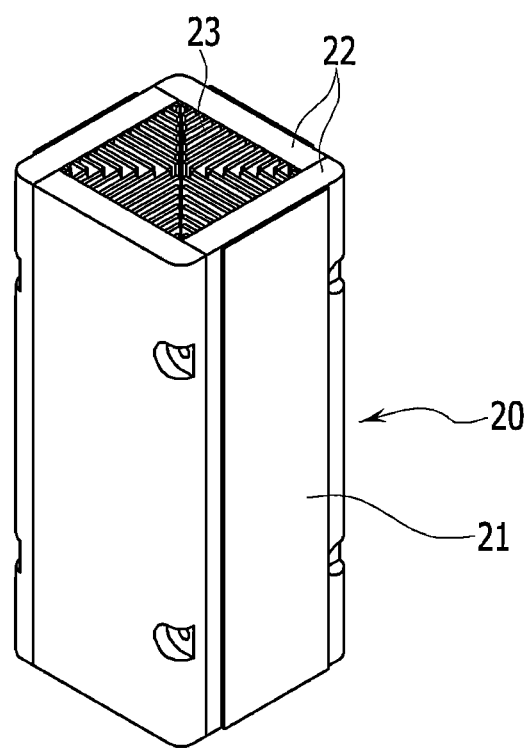
FIG. 4 is a schematic diagram illustrating the cooling temperature adjuster according to the embodiment.

As shown in FIG. 4, in the embodiment, the cooling temperature adjuster 20 has a structure in which the heating plate 22 of the heat exchanger has a hollow quadrangular shape, the heat dissipation fins 23 are installed to be arranged on an inner circumferential surface of the heating plate 22 such that a coolant exchanges heat with the heat dissipation fins 23 while passing through the inside of the heating plate 22, and the heat source 21 is installed on at least one surface of the heating plate 22.

That is, in the embodiment, the heat exchanger of the cooling temperature adjuster 20 has a hollow quadrangular pipe such that a coolant sprayed by the nozzle 32 of the sprayer passes through an empty inside of the heat exchanger. Since the plurality of heat dissipation fins 23 connected to the heating plate 22 are installed to be arranged in the empty inside of the heat exchanger, the coolant passing through the inside of the heating plate 22 of the heat exchanger passes through the heat dissipation fins 23 installed in the heating plate 22 to exchange heat with the heat dissipation fins 23.

In the embodiment, the heating plate 22 may be formed in the housing 12 to have an adequate size to allow all the coolant sprayed by the nozzle 32 of the sprayer to pass through the inside of the heating plate 22. Accordingly, heat of the coolant sprayed by the nozzle 32 may be exchanged while all the coolant passes through the heat exchanger and efficiency in controlling a temperature may be increased.

Also, in the embodiment, the heat exchanger may be formed such that the heating plates 22 may have the same width along a coolant spray direction as shown in FIG. 4. In addition to the above structure, the heating plate 22 may be formed in a parallelepiped shape in which the diameter gradually decreases toward the spray hole 14 at the front end of the housing 12 along the coolant spray direction. In the case of this structure, the coolant passing through the inside of the heating plate 22 remains in a process of passing through an outlet of the heating plate 22 longer, which gradually narrows, in the heating plate 22 such that a heat exchange time between the heat exchanger and the coolant may be further increased.

An arrangement structure of the heat dissipation fins 23 installed in the heating plate 22 may be modified into a variety of shapes.

Also, a sealant for heat insulation may be further installed outside the heat exchanger of the cooling temperature adjuster. The sealant surrounds the heating plate 22 and prevents heat from being transferred to the heat exchanger from the outside. Accordingly, when heat is exchanged between the heat exchanger and the coolant, a heat loss may be minimized. In the embodiment, since the cooling temperature adjuster is installed in the housing such that the heat exchanger is surrounded by the housing 12, the housing 12 may perform a function of the sealant. Particularly, the front end of the housing at which the cooling temperature adjuster is disposed may be formed of a separate heat insulation material unlike the material used for another part of the housing. Accordingly, in an area of the cooling temperature adjuster in which heat exchange is performed, heat insulation may be performed more effectively.

The heat source 21 may include an electric heater which is installed to be attached to an outer surface of the heating plate 22.

The electric heater may be installed on each side surface of the quadrangular heating plate 22 or may be installed on only some of the side surfaces. The electric heater is a structure which converts electrical energy into thermal energy and receives power from the power supply 40 and generates heat energy. The electric heater has, for example, a film shape having a size corresponding to the side surface of the heating plate 22 and may be attached to the side surface of the heating plate 22.

Accordingly, when the electric heater is operated, heat is transferred and applied to the heating plate 22 and heat of the heating plate 22 is transferred to the heat dissipation fins 23 installed in the heating plate 22. Accordingly, the coolant passing through a space between the heat dissipation fins 23 is heated by the heat transferred to the heat dissipation fins 23 such that a temperature thereof increases.

Figure 5:
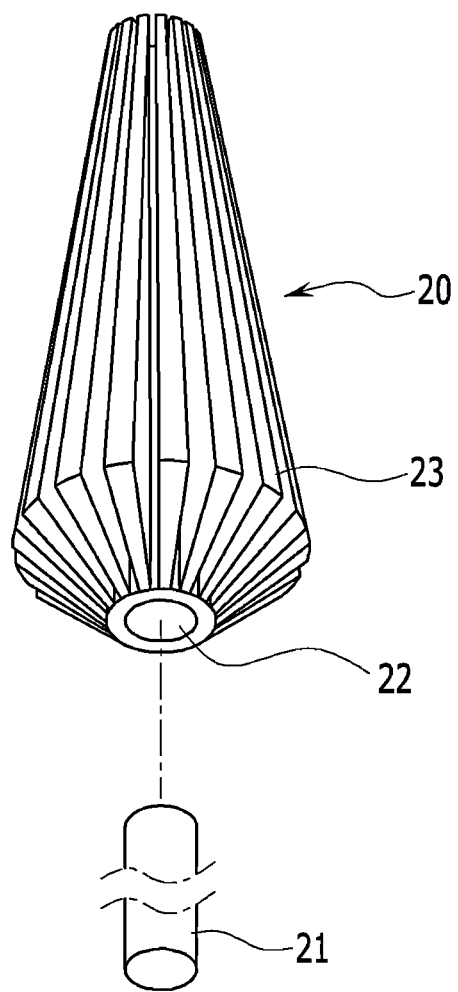
FIG. 5 is a schematic diagram illustrating a cooling temperature adjuster according to another embodiment.

Meanwhile, FIG. 5 illustrates another embodiment of the cooling temperature adjuster 20.

As shown in FIG. 5, the cooling temperature adjuster 20 of the embodiment includes a heat source 21 for heating a coolant and a heat exchanger installed between the heat source 21 and the coolant to transfer heat. Here, the heat exchanger includes the heating plate 22, in which a heat source 21 is installed, and a plurality of heat dissipation fins 23 which are installed in the heating plate 22 and come into contact with the coolant to dissipate heat of the heating plate 22 to the coolant.

In the embodiment, the heating plate 22 of the heat exchanger has a hollow and cylindrical shape and the heat dissipation fins 23 are installed to be arranged along an outer circumferential surface of the heating plate 22 such that heat of the coolant may be exchanged with that of the heat dissipation fins 23 while passing outside the heating plate 22, and the heat source 21 may be inserted to be installed into a center of the heating plate 22.

The heat dissipation fins 23 have a structure of protruding from the heating plate 22, having a plate shape extending lengthwise along a coolant spray direction, and being arranged at intervals to increase a contact area with the coolant. Accordingly, a contact area with the coolant is further increased by the heat dissipation fins 23 so as to maximize heat transfer efficiency.

In the embodiment, in the cooling temperature adjuster 20, heat exchange is performed while the coolant sprayed by the nozzle 32 of a sprayer passes outside the heating plate 22. Since the plurality of heat dissipation fins 23 connected to the heating plate 22 are installed to be arranged outside the heating plate 22, the coolant passing outside the heating plate 22 passes by the heat dissipation fins to exchange heat with the heat dissipation fins 23.

Also, as shown in FIG. 5, in the embodiment, the heat exchanger may have a structure in which a protrusion length of the heat dissipation fins 23 gradually decreases toward the spray hole 14 at the front of the housing 12 along the coolant spray direction such that the heat exchanger may have an overall conic shape along the coolant spray direction. In the case of the above structure, a flow of the coolant passing the heat dissipation fins 23 and flowing through the spray hole 14 may be easily maintained by flexibly connecting a front end of the heat exchanger to the spray hole 14.

An arrangement structure of the heat dissipation fins 23 installed in the heating plate 22 may be modified into a variety of shapes.

The heat source 21 may include a bar-shaped electric heater. Since a hollow groove is formed in a center of the heating plate 22 to install the electric heater therein, the bar-shaped electric heater is inserted into the hollow groove and is coupled with the heating plate 22. The shape or number of the hollow groove formed in the heating plate 22 and the shape or number of the electric heater installed to be inserted in the hollow groove may be variously modified.

Accordingly, when the electric heater is operated, heat is transferred and applied to the heating plate 22 and heat of the heating plate 22 is transferred to the heat dissipation fins 23 installed in the heating plate 22. Accordingly, the coolant passing through a space between the heat dissipation fins 23 is heated by the heat transferred to the heat dissipation fins 23 such that a temperature thereof increases.

The controller 50 includes the temperature measurer 51 for detecting a temperature of a treatment area and a temperature sensor 52 installed in the cooling temperature adjuster 20 to detect a temperature of the cooling temperature adjuster 20 to have a structure in which heat energy of the cooling temperature adjuster 20 or a spray amount of the sprayer is adjusted by comparing a real temperature of the treatment area, a real temperature of the coolant passing through the cooling temperature adjuster 20, and a target cooling temperature with one another.

Accordingly, the controller 50 controls the heat source 21 of the cooling temperature adjuster 20 to adjust a temperature of the coolant while passing through the cooling temperature adjuster 20, such that the treatment area is cooling-anesthetized by spraying the coolant, of which the temperature is ultimately adjusted to comply with a treatment purpose.

Also, the controller 50 further includes the input portion 53 for inputting a setting value and the display portion 54 for externally displaying a signal applied to the controller 50. The display portion 54 may include a display for displaying information and a warning light for displaying a visual warning or an alarm for an aural warning.

The controller 50 includes an equation for controlling a temperature of the heat source 21 of the cooling temperature adjuster 20 therein, calculates a value for controlling the temperature of the heat source 21 by comparing a target cooling temperature with a real temperature value according to the equation, and controls the cooling temperature adjuster 20 according to a result of calculation. The controller 50 may adjust power applied to the heat source 21 installed in the cooling temperature adjuster 20 in the mean of electric feedback control based on the equation included therein. The electric feedback control may include a proportional integral differential (PID) control and a pulsed width modulation (PWM) control. In the embodiment, the controller 50 may perform multiple calculations for the electric feedback control through a plurality of stages. For example, the controller of the embodiment may control a temperature of the heat source by performing two stages of PID calculation using a primary equation and a secondary equation. The equations of the controller and a process of controlling the cooling temperature adjuster therethrough will be described below in more detail.

Also, the controller 50 may use a portable power supply device, for example, a secondary battery as a power supply, but is not limited thereto. The controller 50 may apply a temperature of a coolant and a treatment time, which are necessary and input in advance according to a treatment purpose of a user, for example, local anesthesia, cytoclasis, and the like.

As described above, the heat source 21 of the cooling temperature adjuster 20 is driven by a signal output by the controller 50 and applies calculated heat energy to the coolant to heat the coolant.

The input portion 53 may be connected to the controller 50 and installed outside the housing 12 so as to input a setting value to the controller 50 as necessary. The input portion 53 may input, for example, a target cooling temperature, a coolant spray amount, and the like, according to a treatment purpose to the controller 50.

The input portion 53 may include a treatment input portion and a control input portion. The treatment input portion may be disposed, for example, at an area adjacent to the spray hole 14 to control spraying of the coolant. The treatment input portion may include a spray switch and may determine whether to spray the coolant by turning the spray switch on or off. The control input portion may be disposed to be adjacent to the sprayer or adjacent to the controller. The control input portion may determine a temperature of a coolant or a treatment area to be within a range of −50° C. to 15° C. for local anesthesia. The control input portion may determine a treatment time to be within a range of one second to ten minutes for local anesthesia. The control input portion may include a push button switch and a control switch having an encoder function. When the push button switch of the control switch is turned off and rotated clockwise, a treatment temperature may be increased or a treatment type may be selected. When the push button switch of the control switch is turned off and rotated counterclockwise, the treatment temperature may be decreased or the treatment type may be selected. When the push button switch of the control switch is turned on and rotated clockwise, a treatment time may be increased. When the push button switch of the control switch is turned on and rotated counterclockwise, the treatment time may be decreased. When the treatment type is adjusted by rotating the control switch instead of the treatment temperature, a treatment temperature and a treatment time, which are programmed in advance, may be used in the controller.

The display portion 54 may be disposed to be close to the treatment input portion. The display portion 54 may display a current temperature of a treatment area, a current temperature of a coolant, or current temperatures of the coolant and the treatment area may be displayed through a display and the like. The display portion may display a set point determined by the control input portion, that is, a target temperature of the coolant, a target temperature of the treatment area, or target temperatures of the treatment area and the coolant using the display and the like. The display portion 54 may display a treatment time, a currently remaining time, or the treatment time and the currently remaining time, which are determined by the control input portion. The display portion may perform some or an entirety of functions of the input portion at the same time using a touch screen and the like.

The display of the display portion 54 is installed outside the housing 12 and displays information according to a signal of the controller 50. The display portion 54 may display information related to treatment such as a real temperature value of the treatment area, a temperature value of the coolant, the treatment time, and the like through the display. The warning light and the alarm of the display portion 54 externally display a warning signal applied from the controller 50 when the device is driven by using a visual light or an aural sound. For example, the display portion 54 may warn a user when a temperature of the coolant deviates from a safe range, when a pressure of the coolant deviates from a determined range, when a temperature of the treatment area deviates from a safe range, or when performance of the device, such as power performance, deviates from a determined range.

The temperature sensor 52 may be installed inside or outside the cooling temperature adjuster 20. The temperature sensor 52 may be, for example, a thermistor which detects a temperature through a physical contact. The temperature sensor 52 may be installed at a position as far from the heat source 21 as possible in order to detect an accurate temperature of the coolant which is heat-exchanged through the cooling temperature adjuster 20 and is discharged.

The temperature measurer 51 may be spaced apart from a coolant spray position with respect to the treatment area to measure a temperature using a non-contact method. The temperature measurer 51 may be a non-contact temperature-measuring infrared sensor. The temperature measurer 51 may be disposed at an angle capable of minimizing an effect of the coolant in measuring the temperature of the treatment area. In the embodiment, the temperature measurer 51 may be disposed toward the treatment area while tilting at an angle of 2 to 20° with respect to a coolant spray direction to measure a temperature. Accordingly, heat exchange is performed on the coolant while the coolant passes through the cooling temperature adjuster 20, which is controlled by the controller 50, and the coolant is adjusted to be at a desirable temperature value. The coolant has an adequately adjusted temperature value and then is sprayed on the treatment area such that a degree of risk with respect to epidermal cells of the treatment area, with which the coolant comes into direct contact, may be minimized.

Figure 6:
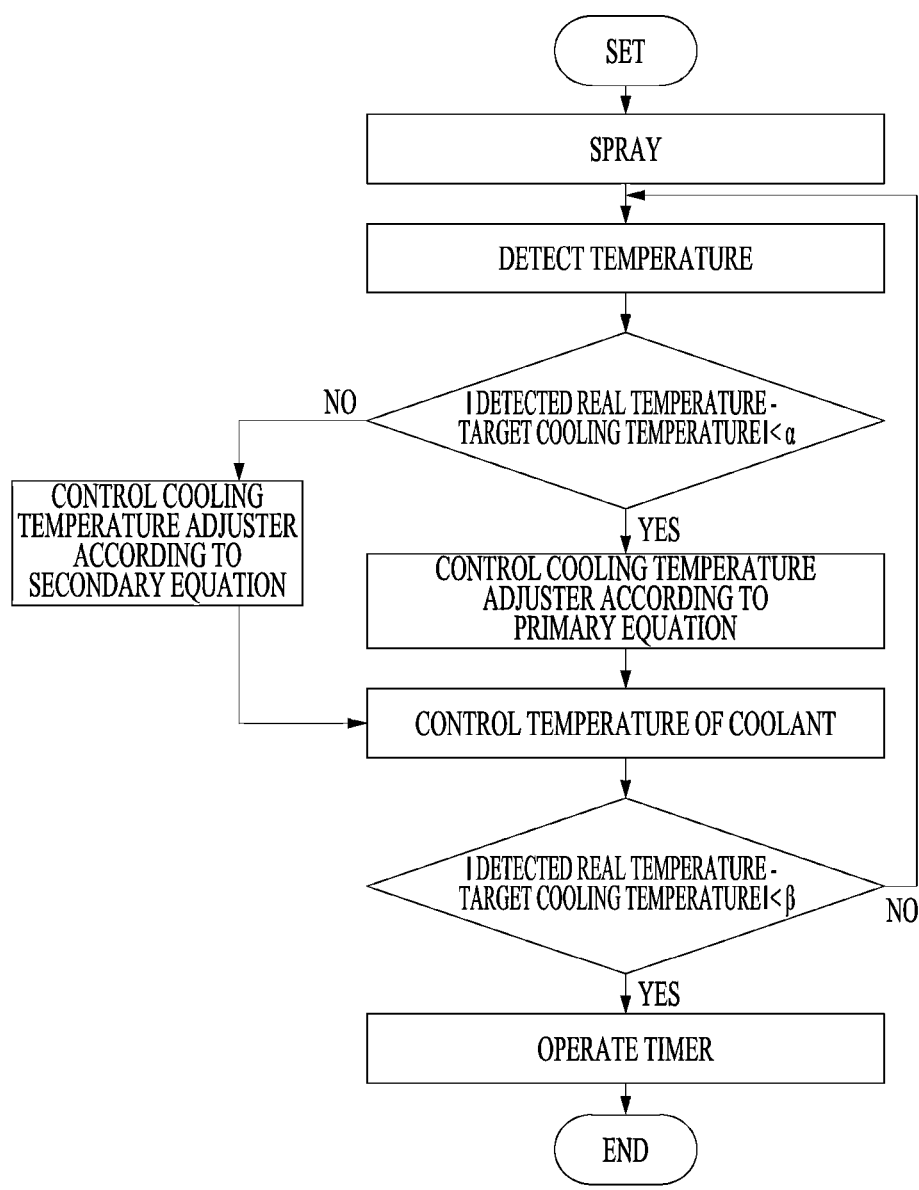
FIG. 6 is a flowchart illustrating a cooling temperature controlling process according to the embodiment.

Hereinafter, a process of controlling a temperature of a coolant according to the embodiment will be described with reference to FIG. 6.

The controlling process according to the embodiment includes setting a target cooling temperature with respect to a treatment area, cooling the treatment area by spraying a coolant thereon, detecting a real temperature of the treatment area, and comparing a detected real temperature value with a target cooling temperature and controlling a temperature of the coolant by adjusting a heat source of a cooling temperature adjuster or a coolant spray amount such that the real temperature value reaches the target cooling temperature.

Before spraying of the coolant, the target cooling temperature is set and the coolant spray amount is adjusted according to a treatment purpose according to a command of the input portion 53. When cooling process of the treatment area starts, the temperature of the coolant supplied from the supplier 30 is adjusted while passing through the cooling temperature adjuster 20 such that the coolant can be provided to the treatment area at a temperature, which is ultimately adjusted in compliance with a treatment purpose. Accordingly, the treatment area may be prevented from being damaged by over cooling.

In the controlling of the temperature, the controller 50 receives power from the power supply and controls the heat source 21 installed in the cooling temperature adjuster 20 according to a real temperature value of the treatment area, which is received from the temperature measurer 51, and a target cooling temperature set through the input portion 53.

Here, the real temperature value may be a temperature value obtained through the temperature measurer 51 or a temperature value of a coolant, which is obtained through the temperature sensor 52 installed in the cooling temperature adjuster.

When an initial value according to the treatment purpose is set, the coolant is sprayed to the treatment area. The coolant passes from the supplier 30 through the cooling temperature adjuster 20 and is sprayed to the treatment area through the spray hole 14 at the front end of the housing 12 to cool the treatment area.

In the process of cooling the treatment area, a real temperature value of the treatment area cooled by the coolant is detected through the temperature measurer 51.

The controller 50 compares the detected real temperature value with the target cooling temperature and controls the temperature of the coolant by adjusting the heat source 21 of the cooling temperature adjuster 20 or the coolant spray amount such that the real temperature value reaches the target cooling temperature.

In more detail, in the temperature controlling process, the controller 50 controls power applied to the heat source 21 of the cooling temperature adjuster 20 in a two-stage process by calculating using PID control through the two equations which are prestored in the controller 50. Accordingly, the temperature of the coolant which passes through the cooling temperature adjuster 20 may be quickly or precisely adjusted through the temperature controlling process. Through the two-stage calculation process, the temperature may be quickly controlled when the real temperature value is far from the target cooling temperature, and the temperature may be precisely controlled when the real temperature value is close to the target cooling temperature.

The temperature controlling process is not limited to the two-stage PID calculation using the primary equation 1 and the secondary equation 2 and may perform three or more-stages of PID calculation as necessary. For example, a temperature of the heat source after cooling is finished may be adequately controlled through three stages of calculation.

Hereinafter, a case of controlling a temperature through the two PID calculation stages using the primary equation 1 and the secondary equation 2 will be described as an example.

Of the preset equations of the controller, the primary equation 1 is for precise temperature control and the secondary equation 2 is for rapid temperature control. In the embodiment, the equations are as follows.

$$P(t) = C_{p,1}\text{error}(t) + C_{i,1}\int_0^t \text{error}(t)dt + C_{d,1}\frac{d(erroe(t))}{dt} \quad \text{Primary Equation (1)}$$

$$P(t) = C_{p,2}\text{error}(t) + C_{i,2}\int_0^t \text{error}(t)dt + C_{d,2}\frac{d(erroe(t))}{dt} \quad \text{Secondary Equation (2)}$$

Here, P(t) is a digital or analog type output value output at a certain time t from the controller, and error (t) is a difference between a temperature measured at the time t and a target cooling temperature. Cp, Ci, and Cd are constants of proportional (P), integral (I), and differential (D), which are used in PID control, respectively.

Here, constants of the primary equation 1 and the secondary equation 2 have different values such that a value of P(t) that is a value obtained by applying the secondary equation 2 may be greater than a value of P(t) obtained by applying the primary equation 1 (for example, Cp, 1<Cp, 2, Ci, 1<Ci, 2, and Cd, 1<Cd, 2).

For example, in the temperature controlling process, the constants Cp, 2, Ci, 2, and Cd, 2 used in the secondary equation 2 are set to be large so as to increase P(t) from same error (t) such that cooling may be quickly performed in an early stage of treatment, and the constants Cp, 1, Ci, 1, and Cd, 1 used in the primary equation 1 are adjusted to be small such that a temperature may be precisely adjusted when error (t) is small.

The controller 50 controls the temperature through PID calculation using an alpha value as a first stage. The controller compares a detected real temperature value with a target cooling temperature and calculates whether an absolute value of the difference between the real temperature value and the target cooling temperature is smaller than an alpha value $\alpha$ that is a predetermined arbitrary range. The alpha value $\alpha$ refers to a primary limit range which recedes from the target cooling temperature. Accordingly, the controller calculates whether the real temperature value deviates from the target cooling temperature more than the alpha value $\alpha$ that is the primary limit through the above process.

Also, when the absolute value of the difference between the real temperature value and the target cooling temperature is smaller than the alpha value $\alpha$, the controller 50 heats the coolant by controlling power which is applied to the heat source 21 of the cooling temperature adjuster 20 according to the primary equation 1 for precise cooling control, which is one of the equations included in the controller.

As the heat source 21 of the cooling temperature adjuster 20 is controlled, heat of the coolant which passes through the cooling temperature adjuster 20 is exchanged with heat energy of the heat source 21. The coolant, which is heated by the heat source 21 such that a temperature thereof increases, is sprayed on the treatment area such that a real cooling temperature of the treatment area is adjusted to approximate to a target cooling temperature.

When the absolute value of the difference between the real temperature value and the target cooling temperature is more than the alpha value $\alpha$ obtained through the calculation process, the controller 50 heats the coolant by controlling power which is applied to the heat source 21 of the cooling temperature adjuster 20 according to the secondary equation 2 for quick cooling control, which is one of the equations included in the controller.

Also, when high-speed cooling is necessary in the early stage, the controller 50 may set the constant of the secondary equation 2 such that power which is applied to the heat source 21 becomes zero. Accordingly, the heat source 21 of the cooling temperature adjuster 20 is not operated such that heat of the coolant is not exchanged with heat of the cooling temperature adjuster 20 and the coolant is sprayed on the treatment area through the spray hole 14 to quickly cool the treatment area. On the other hand, when mild cooling is necessary in the early stage, the constant of the secondary equation 2 may set a power value applied to the heat source 21 such that the temperature of the coolant changes at a speed of, for example, 1° C./sec for relatively slow cooling.

Also, in the controlling of the temperature, when high-speed cooling is necessary in the early stage, a temperature of the cooling temperature adjuster may be decreased in advance by spraying the coolant in advance. Accordingly, the temperature of the cooling temperature adjuster is decreased before treatment such that time consumed for cooling the treatment area may be further reduced to be minimized.

Next, while the heat source 21 is controlled according to the primary equation 1 or the secondary equation 2, the controller calculates whether the real temperature value of the treatment area adequately approaches the target cooling temperature by comparing the real temperature value with the target cooling temperature.

That is, a detected real temperature value is compared with a target cooling temperature and whether an absolute value of the difference between the real temperature value and the target cooling temperature is smaller than a preset arbitrary beta value $\beta$ is calculated. The beta value $\beta$ refers to a secondary limit range which recedes from the target cooling temperature and may be set to be a value closer to a target cooling temperature than the alpha value $\alpha$. Accordingly, the controller calculates whether the real temperature value deviates from the target cooling temperature more than the beta value $\beta$ that is the secondary limit through the above process.

When an absolute value of a difference between the real temperature value and the target cooling temperature is greater than or equal to the beta $\beta$, the cooling temperature adjuster 20 is controlled and the two values are compared by repetitively performing the process. When the absolute value of the difference between the real temperature value and the target cooling temperature is smaller than the beta value $\beta$, that is, when the real temperature value adequately approaches the target cooling temperature, a timer is driven and cooling treatment is completed after a setting time of the timer has passed.

The alpha value $\alpha$ and the beta value $\beta$ may be understood as certain temperature values which are arbitrarily applied to the target cooling temperature. The alpha value $\alpha$ has an absolute value which is relatively greater than the beta value $\beta$, and the beta value $\beta$ refers to an absolute value which is relatively smaller than the alpha value. For example, when the target cooling temperature is −10° C., the alpha value $\alpha$ is 2° C. and the beta value $\beta$ may be set to be 1° C. smaller than 2° C. The alpha value and the beta value $\beta$ are not specified values and may be adequately set according to a treatment purpose.

Through the two stages of PID calculation including a primary calculation process using the primary equation 1 and a secondary calculation process using the secondary equation 2, the real temperature value may be effectively adjusted to the target cooling temperature by performing quick temperature control when the real temperature value is far from the target cooling temperature and performing precise temperature control when the real temperature value is close to the target cooling temperature. In the temperature controlling process of the embodiment, the controller performs PID calculation through the two stages but is not limited thereto and may perform three or more stages of control by further refining the temperature controlling process as necessary.

When the timer is driven or the setting time of the timer has passed, the controller 50 may inform a user that cooling anesthesia of the treatment area is completed by externally displayed notification.

As described above, the coolant experiences heat exchange while passing through the cooling temperature adjuster 20, and thereby the temperature of the coolant is adjusted to a desirable temperature. Accordingly, the temperature of the treatment area cooled by the coolant can be kept within a safe range. Also, as the coolant passes through the cooling temperature adjuster 20 controlled according to a treatment purpose, the temperature of the coolant is adjusted in compliance with the treatment purpose and is sprayed on the treatment area. The increased temperature of the coolant enables smooth start of cooling treatment such that a degree of risk with respect to epidermal cells that comes into direct contact with the coolant may be minimized. When high-speed cooling treatment is necessary in an early stage, the coolant passes through the cooling temperature adjuster 20 in advance before starting the treatment such that a temperature of the cooling temperature adjuster 20 may be adjusted to a temperature according to a treatment purpose. The controller 50 may precisely adjust the temperatures of the coolant and the cooling temperature adjuster 20 using coolant-based heat absorption and heating of the heat source 21 of the cooling temperature adjuster 20 at the same time.

At least one of the disclosed embodiments may be applied to a local cooling anesthesia device, a method of controlling the local cooling anesthesia device, and a cooling temperature adjuster of the local cooling anesthesia device.

Although embodiments have been described, the present invention is not limited thereto, and a variety of modifications may be made without departing from the range of the claims, the detailed description of the present invention, and the attached drawings, which will belong to the scope of the present invention.

What is claimed is:

1. A local cooling anesthesia device, comprising:
   a coolant container configured to store a coolant;
   a nozzle configured to receive the coolant from the coolant container and comprising a nozzle opening configured to generate a sprayed flow of the coolant;
   a sprayer comprising a spray opening, the sprayer configured to output the sprayed flow from the nozzle on a treatment area through the spray opening;
   a temperature measurer configured to detect a temperature of the treatment area; and
   a coolant temperature adjuster comprising a heater configured to adjust a temperature of the sprayed flow flowing through the coolant temperature adjuster,
   wherein the coolant temperature adjuster is interposed between the nozzle and the sprayer and is in fluid communication with the spray opening of the sprayer and is configured to guide the sprayed flow from the nozzle to the sprayer, and
   wherein the heater is configured to adjust the temperature of the sprayed flow according to the temperature of the treatment area detected by the temperature measurer such that the temperature of the treatment area reaches a predetermined temperature.

2. The local cooling anesthesia device of claim 1, wherein the coolant temperature adjuster further comprises a plurality of heat dissipating members, and wherein the plurality of heat dissipating members are projected from the heater and configured to disturb at least part of the sprayed flow and provide heat inside the sprayed flow as the sprayed flow passes by an external surface of the heat dissipating members.

3. The local cooling anesthesia device of claim 2, wherein the heater comprises a heat source and a heating plate, wherein the plurality of heat dissipating members are projected inwardly from the heating plate, and wherein the heat source is configured to provide heat energy to the plurality of heat dissipating members through the heating plate arranged between the heat source and the plurality of heat dissipating members.

4. The local cooling anesthesia device of claim 2, wherein the heater includes a first heating plate and a second heating plate facing the first heating plate, and wherein the plurality of heat dissipating members are arranged between the first heating plate and the second heating plate.

5. The local cooling anesthesia device of claim 1, wherein the coolant temperature adjuster further comprises a plurality of heat dissipating members configured to directly contact the sprayed flow of the coolant flowing therethrough.

6. The local cooling anesthesia device of claim 1, wherein the heater is configured to exchange heat with the sprayed flow of the coolant flowing therethrough.

7. The local cooling anesthesia device of claim 1, further comprising:
   a transfer line connecting the coolant container and the nozzle; and
   a valve installed on the transfer line,
   wherein the valve is configured to control a flow rate of the coolant flowing from the coolant container to the nozzle.

8. The local cooling anesthesia device of claim 1, wherein the nozzle opening comprises a hole having a diameter of about 500 micrometer (μm).

9. The local cooling anesthesia device of claim 1, wherein the local cooling anesthesia device further comprises:
   a first body accommodating the coolant container and a power supply configured to supply power to a controller and extending in a first direction, the controller configured to control the coolant temperature adjuster; and
   a second body accommodating the nozzle, the coolant temperature adjuster and the sprayer and extending in a second direction that is different from and bent with respect to the first direction,
   wherein the second body is connected to the first body with an angle such that the local cooling anesthesia device has a bent shape, and
   wherein the nozzle, the coolant temperature adjuster and the sprayer are arranged in the second direction such that the coolant flows in the coolant temperature adjuster in the second direction that is different from the first direction in which the first body extends.

10. The local cooling anesthesia device of claim 9, wherein an input device electrically connected to the controller is disposed on the first body while a display electrically connected to the controller is disposed on the second body.

11. The local cooling anesthesia device of claim 1, wherein the sprayer is directly connected to the coolant temperature adjuster.

12. The local cooling anesthesia device of claim 1, wherein the sprayer comprises an inlet opposing the spray opening and configured to receive a temperature adjusted sprayed flow from the coolant temperature adjuster, wherein the coolant temperature adjuster comprises a first end configured to receive the sprayed flow from the nozzle and a second end opposing the first end and coupled to the inlet of the sprayer, and wherein a width of the second end is larger than a width of the spray opening.

13. The local cooling anesthesia device of claim 12, wherein the nozzle comprises an outlet configured to output the sprayed flow to the coolant temperature adjuster, and wherein a width of the outlet of the nozzle is larger than the width of the spray opening.

14. The local cooling anesthesia device of claim 1, further comprising a housing accommodating at least the coolant temperature adjuster and the nozzle therein, and wherein at least a portion of the temperature measurer is disposed outside the housing so as to be exposed to the environment.

15. The local cooling anesthesia device of claim 1, further comprising a controller configured to control at least one of the heater or the sprayer, based on comparison of the measured temperature of the treatment area and the temperature of the sprayed flow flowing through the coolant temperature adjuster, so as to adjust at least one of the temperature of the sprayed flow flowing through the coolant temperature adjuster or a spray amount output from the sprayer.

* * * * *